(12) United States Patent
Pearce et al.

(10) Patent No.: US 11,733,157 B2
(45) Date of Patent: Aug. 22, 2023

(54) CABIN AIR SENSOR FOR OZONE DETECTION

(71) Applicant: Honeywell International Inc., Morris Plains, NJ (US)

(72) Inventors: Daniel Pearce, Chard (GB); Richard B. Fox, San Tan Valley, AZ (US); Jan Ludvik, Jesenice (CZ); Ian Kerr, Broadway (GB); John Rogers, Weymouth (GB)

(73) Assignee: Honeywell International Inc., Charlotte, NC (US)

( * ) Notice: Subject to any disclaimer, the term of this patent is extended or adjusted under 35 U.S.C. 154(b) by 494 days.

(21) Appl. No.: 16/921,445

(22) Filed: Jul. 6, 2020

(65) Prior Publication Data

US 2022/0003664 A1    Jan. 6, 2022

(51) Int. Cl.
*G01N 21/33* (2006.01)
*B01D 53/86* (2006.01)
(Continued)

(52) U.S. Cl.
CPC ......... *G01N 21/33* (2013.01); *B01D 53/8675* (2013.01); *B64D 13/02* (2013.01); *B64D 13/06* (2013.01); *G01N 21/05* (2013.01); *G01N 33/0014* (2013.01); *B64D 2013/0685* (2013.01); *G01N 33/0039* (2013.01); *G01N 2021/8578* (2013.01)

(58) Field of Classification Search
CPC ........... G01N 33/0039; G01N 33/0014; G01N 21/05; G01N 21/33; B64D 2013/0625; B64D 2013/0618; B64D 2013/0688; B64D 2013/0685; B64D 2013/0681; B64D 13/04; B01D 53/8675
See application file for complete search history.

(56) References Cited

U.S. PATENT DOCUMENTS

| 4,302,206 | A | * | 11/1981 | Profeta | ................. | G01N 21/33 436/164 |
| 6,096,557 | A | | 8/2000 | Tanaka et al. | | |

(Continued)

FOREIGN PATENT DOCUMENTS

| CN | 206248627 U | 6/2017 |
| EP | 3183559 A1 | 6/2017 |

OTHER PUBLICATIONS

Yoshinobu Aoyagi, "High-Sensitivity Ozone Sensing Using 280 nm Deep Ultraviolet Light-Emitting Diode for Detection of Natural Hazard Ozone", May 13, 2012 (Year: 2012).*

(Continued)

*Primary Examiner* — Maurice C Smith
(74) *Attorney, Agent, or Firm* — Shumaker & Sieffert, P.A.

(57) ABSTRACT

A method of measuring a gas concentration is described. The method comprises illuminating, with a light source, a volume of space that includes a gas and measuring, with a detector, a first illumination level of the volume of space. The method further comprises determining, via a processor, a gas concentration in the volume of space based on the measured first illumination level, where the volume of space is configured to be in fluid communication with a gas recirculation flow path including a catalyst, the catalyst configured to substantially remove the gas from the volume of space.

20 Claims, 3 Drawing Sheets

(51) Int. Cl.
*B64D 13/02* (2006.01)
*B64D 13/06* (2006.01)
*G01N 33/00* (2006.01)
*G01N 21/05* (2006.01)
*G01N 21/85* (2006.01)

(56) References Cited

U.S. PATENT DOCUMENTS

| | | | |
|---|---|---|---|
| 9,625,372 | B2 | 4/2017 | Bilenko et al. |
| 10,175,213 | B2 * | 1/2019 | Dimick .................. G01N 21/31 |
| 10,272,169 | B2 | 4/2019 | Lin et al. |
| 10,295,457 | B1 | 5/2019 | Ocheltree |
| 10,339,778 | B1 * | 7/2019 | Birnkrant ............. G01K 15/005 |
| 2005/0087072 | A1 * | 4/2005 | Wodjenski ......... B01D 53/0446 96/111 |
| 2006/0011844 | A1 | 1/2006 | Oka et al. |
| 2011/0201123 | A1 | 8/2011 | Watson et al. |
| 2019/0100318 | A1 * | 4/2019 | Space .................... B01D 53/72 |

OTHER PUBLICATIONS

Bhangar et al., "Ozone Levels in Passenger Cabins of Commercial Aircraft on North American and Transoceanic Routes", Environmental Science & Technology, vol. 42, No. 11, Jun. 1, 2008, pp. 3938-3943, XP055614659, US ISSN: 0013-936X, 6 pp.

Extended Search Report from counterpart European Application No. 21170288.1, dated Sep. 30, 2021, 8 pp.

Response to Extended Search Report dated Sep. 30, 2021, from counterpart European Application No. 21170288.1, filed Nov. 10, 2021, 36 pp.

U.S. Appl. No. 16/897,076, Honeywell International, Inc. (Inventors: White et al.), filed Jun. 9, 2020.

Notice of Intent to Grant and Text Intended to Grant from counterpart European Application No. 21170288.1 dated Apr. 19, 2023, 9 pp.

* cited by examiner

CABIN AIR SENSOR FOR OZONE DETECTION

STATEMENT REGARDING FEDERALLY SPONSORED RESEARCH OR DEVELOPMENT

This invention was made with Government support under 113109 awarded by UK ATI (United Kingdom Aerospace Technologies Institute). The Non-US Government may have certain rights in the invention.

TECHNICAL FIELD

The present disclosure relates to systems and techniques for gas-concentration detection.

BACKGROUND

An environmental control system provides pressurized air to a cabin of an aircraft. This pressurized air may be supplied from a variety of sources, such as bleed air from an engine, a cabin air compressor (CAC), or an auxiliary power unit (APU). The pressurized air may include contaminants, including gas contaminants

SUMMARY

Gas-concentration systems and detection techniques described herein may reliably measure a concentration of a gas contaminants by reducing detector drift, thermally induced noise, and noise due to vibration, humidity, pressure and pressure changes.

In some examples, the disclosure describes a method of measuring a gas concentration, the method comprising: illuminating, with a light source, a volume of space that includes a gas; measuring, with a detector, a first illumination level of the volume of space; and determining, via a processor, a gas concentration in the volume of space based on the measured first illumination level, wherein the volume of space is configured to be in fluid communication with a gas recirculation flow path including a catalyst, the catalyst configured to substantially remove the gas from the volume of space.

In some examples, the disclosure describes a gas-concentration measurement system comprising: an ultra-violet (UV) illumination source configured to illuminate a volume of space, wherein the volume is in fluid communication with a gas inlet and a gas outlet, wherein the gas inlet and the gas outlet are configured to allow a gas to flow through the volume; a UV detector configured to measure an illumination level within the volume; and a gas recirculation flow path configured to be in fluid communication with the volume of space and including a catalyst, the catalyst configured to remove the gas from the volume of space during measurement of the illumination of the volume.

In some examples, the disclosure describes a gas-concentration measurement system comprising: a light source configured to illuminate a volume of space including a gas; a light detector configured to measure an amount of light from the light source after the light has propagated through a portion of the volume of space including the gas; and a catalyst configured to remove the gas from the volume during measurement of the light from the light source.

The details of one or more examples are set forth in the accompanying drawings and the description below. Other features, objects, and advantages will be apparent from the description and drawings, and from the claims.

BRIEF DESCRIPTION OF THE FIGURES

The details of one or more examples are set forth in the accompanying drawings and the description below. Other features, objects, and advantages will be apparent from the description and drawings, and from the claims.

DETAILED DESCRIPTION

Figure 1:
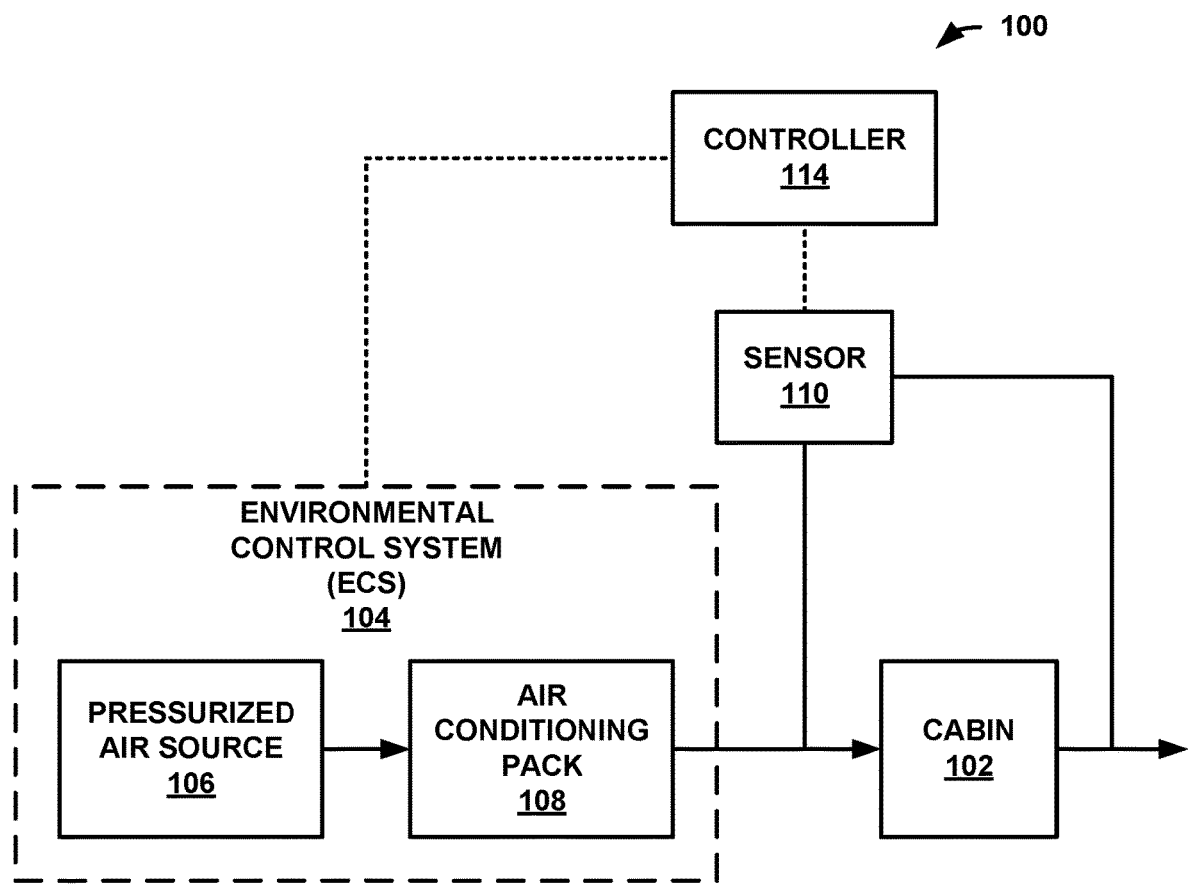
FIG. 1 is a diagram illustrating an example system for supplying clean, pressurized air to a cabin of an aircraft, in accordance with techniques of the present disclosure.

In general, an environmental control system of an aircraft may supply clean, pressurized air to a cabin of the aircraft based on regulations established by regulatory agencies, such as the Federal Aviation Administration (FAA). These regulations include limits on contaminant gases and compounds such as ozone. For example, FAA AC 120-38 provides guidance on 14 C.F.R. § 121.578, providing limits on the concentration of ozone in the aircraft cabin based on flight levels and the time above certain flight levels. The ozone gas concentration limit is 250 parts-per-billion (ppb) at flight level 320, e.g., a barometric altimeter indicating 32,000 feet, for any amount of time, and the ozone gas concentration limit is 100 ppb for flight level 270 as a time-weighted average for each flight segment that exceeds 4 hours and includes flight above flight level 270. Currently, there is no regulatory mandate to directly measure ozone in an aircraft cabin, and the regulations above are based on assumed and/or modeled levels of ozone gas concentration in the atmosphere at particular flight levels from which an aircraft draws cabin air. Bench-top ozone sensors are not airworthy, partly due to the volatility of ozone and partly due to relatively low concentrations of ozone causing health effects necessitating an increased sensitivity to measure low ozone concentrations. For example, bench-top ozone sensors are not ruggedized with respect to vibration, temperature and temperature changes, pressure and pressure changes, and humidity, to provide accurate measurements of ozone concentrations at or near regulatory limits.

According to various embodiments described herein, a gas-concentration system and method for measuring ozone concentration substantially near regulatory limits on an aircraft. In examples, a gas-concentration may be measured and/or determined based on light scattering and/or absorption of light, e.g., ultraviolet (UV) light. In examples, a gas-concentration system may include a temperature-controlled UV light source, e.g., a UV light emitting diode (UV LED) and a temperature controlled light detector. Temperature control of both the light source and the detector may reduce measured ozone signal drift and thermal electrical noise which interferes with ozone measurement signal quality in both the UV LED source and the solid state detector, thereby increasing the accuracy of gas-concentration measurements and ruggedizing the system for aerospace applications in which the system may be exposed to a large range of temperatures and large temperature changes with respect to time.

The system may include a housing defining a volume of space through which a gas may flow via an inlet and an outlet and through which UV light may propagate from the UV LED to the UV detector, e.g., a gas chamber. A gas concentration may be determined based on the amount of light received by the detector and the atmospheric pressure within the sample chamber, e.g., a sample light level or a sample illumination level. The system may include a pressure sensor configured to measure atmospheric pressure within the sample chamber, e.g., in order to correct ozone concentrations to a reference level, such as sea level. In some examples, the system may be mounted within the pressure vessel of the aircraft, and the system may be vented to atmosphere and the pressure within the sample chamber may vary from 1,013 hectopascal (hPa) at 0 ft altitude to 697 hPa at 10,000 ft cabin altitude. In some examples, is the system may be mounted outside the pressure vessel and the atmospheric pressure can be as low as 111 hPa at 50,000 ft altitude. In some examples, the system may additionally measure a baseline light level by eliminating, removing, or substantially reducing the gas, e.g., ozone, via catalyst recirculated through the gas chamber and collecting a measurement of light from the UV LED by the UV detector. The gas concentration may be additionally based on the baseline light level or baseline illumination level, for example, as a comparison of the baseline illumination level and the sample illumination level. In examples, the housing may be made of gas-inert, e.g., ozone-inert materials and/or coated with ozone-inert coatings. In addition, the housing may be made of, lined with, or coated with, light reflecting materials. For example, the housing may be coated with ozone-inert and UV-reflecting quartz. In some examples, the measurement system may include solid-state components packaged within the housing to reduce measurement variation when subjected to aerospace vibration levels. For example, the UV LED and UV detector may be solid state components mounted on a rigid tube containing the sample chamber to maintain measurement geometry during and after take-off and landing as well as during and after turbulence during a flight segment, or during an emergency landing. In some examples, the system may be configured to withstand g-forces of 3.0 g or more in the upward direction, 9.0 g or more in the forward direction, 3.0 g or more in the sideward direction, 6.0 g or more in the downward direction, and 1.5 g or more in the rearward direction, e.g., such as during emergency landing conditions.

FIG. 1 is a diagram illustrating an example system 100 for supplying clean, pressurized air to a cabin 102 of an aircraft. Cabin 102 includes an internal environment that houses occupants. During flight, these occupants produce one or more contaminants, such as carbon dioxide and water vapor.

System 100 includes an environmental control system (ECS) 104. ECS 104 is configured to supply clean, pressurized air to cabin 102. ECS 104 includes at least one pressurized air source 106. Pressurized air source 106 is configured to generate pressurized air for use in cabin 102. For example, when the aircraft is on the ground, air pressure outside the aircraft may be similar to or the same as air pressure within cabin 102. However, once the air is at higher elevations, the air pressure outside the aircraft may be significantly lower than an air pressure required for cabin 102, such that pressurized air source 106 may supply cabin 102 with pressurized air. Pressurized air source 106 may include a variety of air sources including, but not limited to, a bleed air source (e.g., one of more compression stages of a gas turbine engine), a load compressor (e.g., driven directly by an auxiliary power unit), a stand-alone pressurized air source as cabin air compressors (e.g., driven by electricity from an auxiliary power unit), or any other air source capable of supplying air with a sufficiently high pressure so as to pressurize cabin 102. ECS 104 includes at least one air conditioning pack 108. In the process of compressing the air, pressurized air source 106 may heat the air to a relatively high temperature that is not suitable for direct discharge into cabin 102. Air conditioning pack 108 is configured to receive pressurized air from pressurized air source 106 and cool the pressurized air. In addition, air conditioning pack 108 may include air filtration and/or gas contaminant removal systems.

System 100 includes at least one gas-concentration sensor 110. Gas-concentration sensor 110 is configured to measure a concentration of a gas contained within air flowing into or out of cabin 102. Gas-concentration sensor 110 may be configured to measure the concentration of gas contaminants, such as ozone, during flight at different elevations or flight levels, and/or while the aircraft is on the ground. In the examples shown, gas-concentration sensor may measure the gas-concentration of air entering cabin 102, discharged from cabin 102, or both. Generally, gas-concentration sensor 110 may be configured and/or positioned at any location sufficient to provide an accurate representation of the gas-concentration of a contaminant in cabin 102.

System 100 includes controller 114. Controller 114 is communicatively coupled gas-concentration sensor 110 and ECS 104, and may be configured to receive measurements from gas-concentration sensor 110 and send control signals to one or more systems of ECS 104, such as pressurized air source 106 and/or air conditioning pack 108. Controller 114 may include any of a wide range of devices, including processors (e.g., one or more microprocessors, one or more application specific integrated circuits (ASICs), one or more field programmable gate arrays (FPGAs), or the like), servers, desktop computers, notebook (i.e., laptop) computers, tablet computers, and the like.

Controller 114 is configured to control ECS 104 to maintain adequate conditions within the internal environment of cabin 102, such as for personal comfort or required by law or industry standard. For example, controller 114 may be configured to control a pressure, temperature, humidity, air flow rate, or other ambient conditions of cabin 102 at various aircraft conditions, such as ground operation, passenger loading, take-off, cruising, descent, and landing. In particular, regulatory agencies, such as the FAA, may establish gas-concentration levels regarding air supplied to a cabin of an aircraft. As such, controller 114 is configured to control ECS 104 to supply clean, pressurized air to cabin 102 based on the gas-concentration limits established by the regulatory agencies.

Controller 114 is configured to receive gas-concentration measurements from gas-concentration sensor 110. Controller 114 may determine a concentration measurement that includes a concentration tolerance of gas-concentration sensor 110. Controller 114 may be configured to determine whether a gas-concentration measurement of a contaminant in cabin 102 exceeds a concentration threshold. The concentration threshold may correspond to a maximum allowed gas-concentration for the particular contaminant.

In response to determining that the gas-concentration measurement exceeds the gas-concentration threshold, controller 114 may be configured to control one or more contaminant removal system, e.g., via air conditioning pack 108. For example, in response to determining that the gas-concentration of ozone exceeds an ozone threshold in the cabin, controller 114 may cause cabin air to be recirculated through a contaminant removal system including an ozone catalyst.

Figure 2:
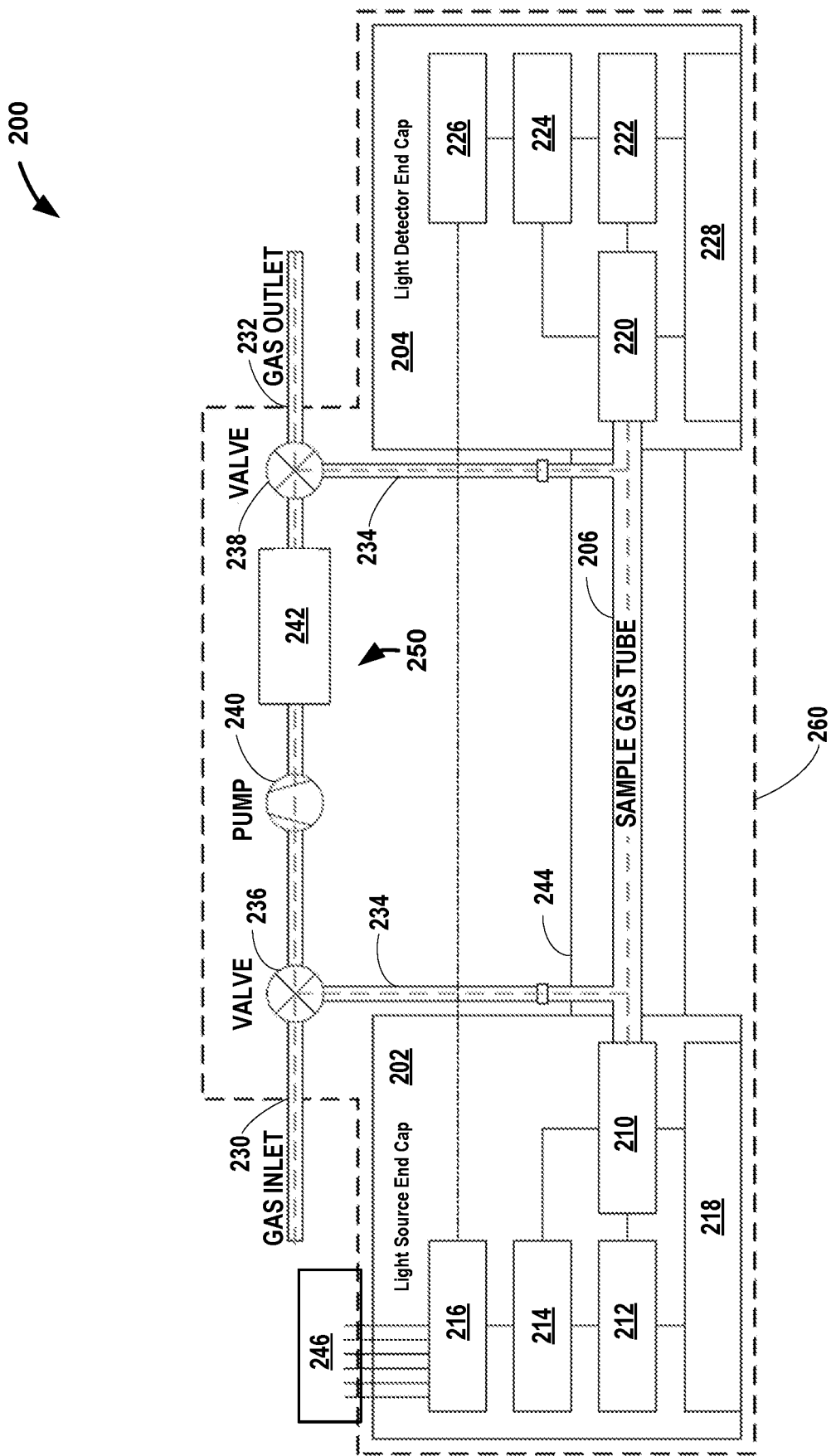
FIG. 2 is a diagram illustrating an example gas-concentration sensor, in accordance with techniques of the present disclosure.

FIG. 2 is a diagram illustrating an example gas-concentration sensor 200, in accordance with techniques of the present disclosure. In the example shown, gas-concentration sensor 200 includes light source end cap 202, light detector end cap 204, sample gas tube 206, and housing 260.

In the example shown, light source end cap 202 includes light source 210, temperature regulator 212, controller 214, interface 216, and heat sink 218. Light source 210 may be configured to emit UV light. Light source 210 may be an incandescent light source, a fluorescent light source, a halogen light source, a gas discharge light source, a thermal light source, a solid-state lights source, a laser, a LED, and the like. In the example shown, light source 210 is a UV LED configured to emit UV light illuminating sample gas tube 206. In some examples, light source 210 may be configured to emit at least partially collimated light and/or include collimating optical elements configured to at least partially collimate light emitted by light source 210. Light source 210 may be thermally coupled to temperature regulator 212.

In some examples, temperature regulator 212 may be configured to maintain a predetermined temperature and/or temperature range of light source 210. For example, a temperature sensor (not shown) may be connected to light source 210 and configured to measure the temperature of light source 210. The temperature sensor may be connected to controller 214 and may be configured to communicate the measured temperature of light source 210 to controller 214. Controller 214 may be configured to determine a difference temperature based on the measured temperature and the predetermined temperature and/or predetermined temperature range. Controller 214 may be connected to temperature regulator 212 and may be configured to cause temperature regulator 212 to change the temperature of light source 210 based on the difference temperature. In some examples, controller 214 may cause temperature regulator 212 to change the temperature of light source 210 based on the magnitude of the difference temperature being greater than a threshold value. In some examples, controller 214 may be configured to determine a correction temperature, e.g., via a proportional-integral-derivative (PID) algorithm, or any other algorithm, and based on any of the measured temperature, predetermined temperature, and difference temperature. For example, controller 214 may include a PID controller configured to execute a control algorithm, such as a PID algorithm, to determine the correction temperature and cause temperature regulator 212 to change the temperature of light source 210 based on the correction temperature. Temperature regulator 212 may be any type of heater and/or cooler capable of heating and/or cooling light source 210. In some examples, temperature regulator 212 may be a thermoelectric cooler (TEC). In some examples, light source 210 may emit an illumination level and/or wavelength content that depends on the temperature of light source 210. For example, the brightness and/or spectral content of UV LED 210 may vary depending on the temperature of UV LED 210. Temperature regulator 212 may stabilize the illumination level and/or spectral content of light source 210 via maintaining a predetermined temperature and/or temperature range of light source 210.

Controller 214 may be an electronic controller including processing circuitry. For example, controller 214 may include a processor and computer-readable storage medium encoded with instructions for causing temperature regulator 212 to change the temperature of light source 210 based on the difference temperature. In some examples, controller 214 may be connected to interface 216. Interface 216 may be connected to interface 226 and/or sensor interface 246, enabling communication between controller 214 of light source end cap 202, controller 224 of light detector end cap 204, and external devices via sensor interface 246.

In the example shown, heat sink 218 may be configured to remove heat from light source 210, e.g., via TEC 212.

In the example shown, light detector end cap 204 includes light detector 220, temperature regulator 222, controller 224, interface 226, and heat sink 228. Light detector 220 may be configured to detect UV light. Light detector 220 may be photoconductor, a photoresistor, a photovoltaic device, a photocell, a phototransistor, a photodiode, and the like. In the example shown, light detector 220 is a UV photodiode configured to detect an illumination level of UV light after the UV light has propagated through sample gas tube 206. In some examples, light detector 220 may include light collecting optical elements configured to at least partially image the light onto a UV photodiode, e.g., a lens. Light detector 220 may be thermally coupled to temperature regulator 222.

In some examples, temperature regulator 222 may be configured to maintain a predetermined temperature and/or temperature range of light detector 220. For example, a temperature sensor (not shown) may be connected to light detector 220 and configured to measure the temperature of light detector 220. The temperature sensor may be connected to controller 224 and may be configured to communicate the measured temperature of light detector 220 to controller 224. Controller 224 may be configured to determine a difference temperature based on the measured temperature and the predetermined temperature and/or predetermined temperature range. Controller 224 may be connected to temperature regulator 222 and may be configured to cause temperature regulator 222 to change the temperature of light detector 220 based on the difference temperature. In some examples, controller 224 may cause temperature regulator 222 to change the temperature of light detector 220 based on the magnitude of the difference temperature being greater than a threshold value. In some examples, controller 224 may be configured to determine a correction temperature, e.g., via a proportional-integral-derivative (PID) algorithm, or any other algorithm, and based on any of the measured temperature, predetermined temperature, and difference temperature. For example, controller 224 may include a PID controller configured to execute a control algorithm, such as a PID algorithm, to determine the correction temperature and cause temperature regulator 222 to change the temperature of light detector 220 based on the correction temperature. Temperature regulator 222 may be any type of heater and/or cooler capable of heating and/or cooling light detector 220. In some examples, temperature regulator 222 may be a TEC. In some examples, light detector 220 may emit an illumination level and/or wavelength content that depends on the temperature of light detector 220. For example, the noise level and responsivity of UV photodiode 220 may vary depending on the temperature of UV photodiode 210. Temperature regulator 222 may stabilize the noise and/or responsivity of light detector 220 via maintaining a predetermined temperature and/or temperature range of light detector 220. In some examples, the predetermined temperature and/or temperature range of light detector 220 may be different from the predetermined temperature and/or temperature range of light source 210. In some examples, the predetermined temperature and/or temperature range of either one or both of light detector 220 and light source 210 may be less than the ambient temperature.

Controller 224 may be an electronic controller including processing circuitry. For example, controller 224 may include a processor and computer-readable storage medium encoded with instructions for causing temperature regulator 222 to change the temperature of light detector 220 based on the difference temperature. In some examples, controller 226 may be connected to interface 226. Interface 226 may be connected to interface 216 and/or sensor interface 246 as described above, enabling communication between controller 224 of light detector end cap 204, controller 224 of light source end cap 202, and external devices via sensor interface 246.

In the example shown, heat sink 228 may be configured to remove heat from light detector 220, e.g., via TEC 222.

In some examples, temperature regulators 212, 222 may be controlled by one or more external device(s) via sensor interface 246. For example, interface 246 may be communicatively connected to temperatures sensors (not shown) connected to light source 210 and light detector 220 and temperature regulators 212 and 222. One or more external devices may be configured to cause, via sensor interface 246, temperature regulators 212 and 222 to change the temperature of light source 210 and light detector 220, respectively, based on respective difference temperatures. In other words, gas-concentration sensor 200 may not include any of controllers 214, 224 and interfaces 216, 226. One or more external devices may control the temperature and illumination level of light source 210 and may control the temperature of light detector 220 and receive a signal from light detector 220 based on an illumination level detected by light detector 220.

In the example shown, sample gas tube 206 may be positioned between light source 210 and light detector 220. For example, sample gas tube 206 may be a tube having an inner cross-sectional area, a wall thickness, a length, and may be configured to allow a gas to flow through the tube. In some examples, sample gas tube 206 may be a housing, e.g., a gas housing, defining a volume of space within which a gas may be contained or through which a gas may flow, e.g., sample gas tube 206 may be a housing configured to constrain a gas to flow through the volume of space defined by the housing. Sample gas tube 206 may be a hollow tube shape having a circular cross-sectional shape, a rectangular cross-sectional shape, or any other suitable shape. In some examples, light source 210 and light detector 220 may be within sample gas tube 206. In some examples, sample gas tube 206 may include portions at least partially transparent to light emitted by light source 210 such that light source 210 may emit light into sample gas tube 206 and light detector 220 may receive the light emitted into sample gas tube 206. Sample gas tube 206 may be made of any suitable material, including metal, plastic, polymeric materials, glass, and the like. In some examples, at least the inside surfaces of sample gas tube 206 may be gas-inert, e.g., ozone inert. For example, ozone may oxidize most metals.

Sample gas tube 206, whether made of metal or another material, may include a coating or lining of an ozone inert material such as quartz at least on its inner surfaces. For example, ozone may be unstable and decay into ordinary oxygen. Ozone may have a half-life that varies with atmospheric conditions such as temperature, humidity, and air movement. Therefore, in some examples an ozone inert material and/or coating within sample gas tube 206 may improve preservation of the concentration of ozone for measurement while ozone gas is within and/or flows through sample gas tube 206. In some examples, the sample gas tube may be made of and/or coated with an ozone inert material that also has light reflecting properties with respect to light emitted by light source 210. For example, sample gas tube 206 may be coated with quartz at least on its inner surfaces which may both reduce depletion of ozone being measured and reduce signal losses of the light used to measure the ozone, e.g., by reducing losses of the light at the sidewalls from absorption by the sidewalls or transmission through the sidewalls. In some examples, sample gas tube 206 may be disposed within tube housing 244.

In the example shown, housing 260 may include light source end cap 202, light detector end cap 204, and sample gas tube 206 and may provide structure for mounting and positioning light source 210, light detector 220, and sample gas tube 206. In the example shown, housing 260 may include gas inlet 230 and gas outlet 232, which may be configured to be in fluid communication with sample gas tube 206 via conduits 234. Housing 260 may also include inlet valve 236, outlet valve 238, pump 240. Pump 240 may be configured to move a gas through conduits 234 and sample gas tube 206. In some examples, pump 240 may be configured to stop a flow of gas during measurement of the gas, e.g., during illumination of sample gas tube 206 by light source 210 and detection of the light by light detector 220. In some examples, measurement may occur while the gas is flowing within sample gas tube 206. In the example shown, housing 260 is configured to provide a flow path for a gas, e.g., via gas inlet 230, conduits 234, sample gas tube 206, and gas outlet 232. In some examples, the flow path further includes gas recirculation flow path 250.

In the example shown, housing 260 may include gas recirculation flow path 250, which may be in fluid communication with conduits 234. In the example shown, gas recirculation flow path 250 includes pump 240 and catalyst 242 and is connected to conduits 234 via valves 236 and 238. In some examples, catalyst 242 is configured to remove a gas from sample gas tube 206. For example, valve 236 may close, or shut off, fluid communication between gas inlet 230 and conduits 234, and may open fluid communication between gas recirculation flow path 250 and conduits 234. Valve 238 may close, or shut off, fluid communication between gas outlet 232 and conduits 234, and may open fluid communication between gas recirculation flow path 250 and conduits 234. For example, conduits 234, sample gas tube 206, and gas recirculation flow path 250 may define a closed-loop recirculation flow path for the gas. Pump 240 may cause movement of gas through gas recirculation flow path 250, conduits 234, and sample gas tube 206. At least a portion of catalyst 242 may come into fluid communication with the gas via movement of the gas through gas recirculation flow path 250, and catalyst 242 may catalyze a reaction to remove at least a portion of the gas, e.g., via conversion of ozone gas to oxygen. In some examples, catalyst 242 may remove substantially all, e.g., to less than 1 ppb, of a gas, e.g., ozone gas, from sample gas tube 206. A baseline measurement may be determined with the ozone removed from sample gas tube, e.g., light detector 220 may detect a baseline illumination level of light propagating through sample gas tube 206 emitted by light source 210 into sample gas tube 206 with ozone removed. Valve 236 and valve 238 may close, or shut off, fluid communication with gas recirculation flow path 250 and open fluid communication between gas inlet 230, gas outlet 232, and conduits 234. A gas, e.g., ozone, may flow into and through sample gas tube 206 having a concentration representative of the concentration of ozone within a volume of interest, e.g., the cabin of an aircraft. A measurement may be determined with the ozone present in sample gas tube 206, e.g., light detector 220 may detect a sample illumination level of light propagating through sample gas tube 206 emitted by light source 210 into sample gas tube 206 with ozone present.

Housing 260 may be configured to house and protect the components of gas-concentration sensor 200. For example, gas-concentration sensor 200 may operate on a vehicle, such as a motor vehicle, and aircraft, a watercraft, and the like. Housing 260 may be configured to maintain a measurement geometry, such as the alignment of light source 210 and light detector 220, during baseline and/or sample illumination detection under adverse environmental conditions, such vehicle operating conditions, e.g., takeoff, landing, and during flight, for an aircraft. Housing 260 may be further configured to protect the quartz lining of sample gas tube 206, conduits 234, and/or gas recirculation flow path 250 from breaking during adverse environmental conditions, or otherwise protect the quartz lining from mechanical stress and/or degradation associated with adverse environmental conditions. Housing 260 may further be configured to house and protect light source 210, light detector 220, controllers 214 and 224, sample gas tube 206, recirculation flow path 250, pump 240, valves 236 and 238, fluid inlet 230, and fluid outlet 232 from mechanical stress associated with the adverse environmental conditions. Adverse environmental conditions may include flight environmental conditions. For example, adverse environmental conditions may include any of a vibration, such as associated with takeoff, landing, and during flight for an aircraft, or vibrations associated with a motor vehicle or watercraft. Adverse environmental conditions may include elevated or reduced atmospheric pressures, such as atmospheric pressures less than or equal to 1,013 hPa (e.g., 1 atm), less than or equal to 700 hPa, less than or equal to 120 hPa, or atmospheric pressures as low as 111 hPa, or lower in some examples. Adverse environmental conditions may include temperatures less than 50 degrees Fahrenheit (F.), less than 32 degrees F., less than 0 degrees F., less than −40 degrees F., or lower, in some examples. Adverse environmental conditions may further include acceleration forces, e.g., g-forces, such as acceleration forces greater than or equal to 1.5 g, greater than or equal to 3 g, or greater than or equal to 9 g.

Figure 3:
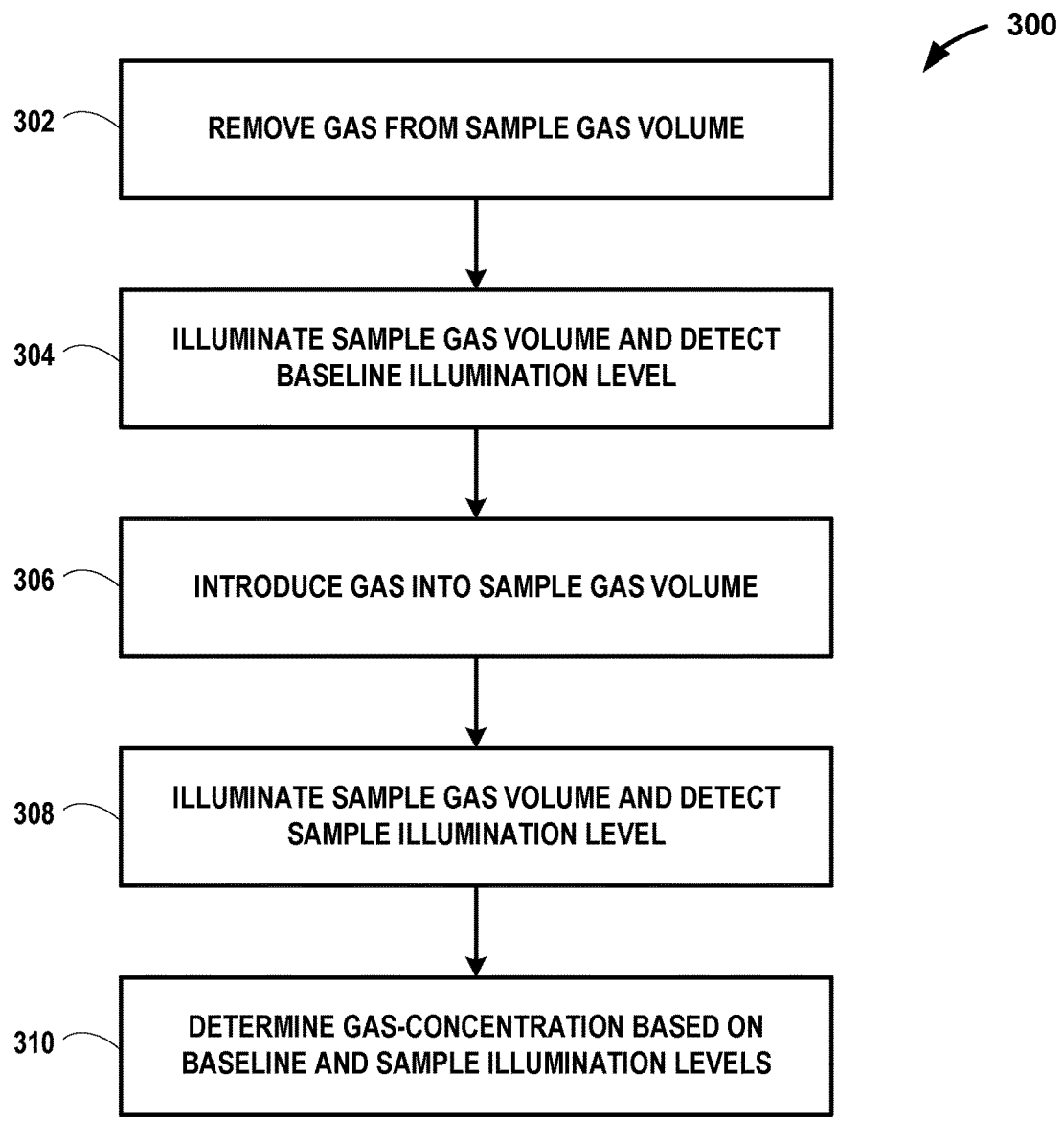
FIG. 3 is a flowchart of a method for measuring a gas-concentration, in accordance with techniques of the present disclosure.

FIG. 3 is a flowchart of a method 300 for measuring a gas-concentration, in accordance with techniques of the present disclosure. While method 300 is described with reference to gas-concentration sensor 200, in other examples, the method 300 may be used with other sensors.

A gas may be removed from a sample gas volume (302). For example, gas-concentration 200 may include a catalyst 242, e.g., a catalytic scrubber, and ozone may be removed from sample gas tube 206 via catalyst 242. A controller, such as light source controller 214, light detector controller 224, and/or an external device in communication with gas-concentration sensor 200 via sensor interface 246, may cause valves 236 and 232 to close and/or shut off gas inlet 230 and gas outlet 232 from fluid communication with conduits 234 and open gas recirculation flow path 250 to be in fluid communication with conduits 234. Gas recirculation flow path 250 may include catalyst 242. The controller may cause pump 240 to circulate air containing the gas, e.g., ozone, through gas recirculation flow path 250, conduits 234, and sample gas tube 206 thereby causing the ozone gas to come into fluid communication with catalyst 242. Catalyst 242 may remove ozone via chemical reaction converting ozone to oxygen. Catalyst 242 may remove substantially all of the ozone in sample gas tube 206, e.g., to negligible ozone-concentration levels.

The sensor may illuminate a sample gas volume and detect a baseline illumination level with the gas removed, e.g., a "zero-gas" illumination level (304). For example, a controller, such as light source controller 214 and/or an external device in communication with light source 210 via sensor interface 246 may cause light source 210 to emit light into sample gas tube 206. A controller, such as detector controller 224 and/or an external device in communication with light detector 220 via sensor interface 246 may cause light detector 220 to measure an illumination level of sample gas tube 206, e.g., a baseline illumination level with ozone removed. In some examples, the controller may receive a signal from light detector 220 proportional to the baseline illumination level of sample gas tube 206 with ozone substantially removed, and the controller may store the baseline illumination level in memory. In some examples, the baseline illumination level may be detected during flight conditions. Housing 260 may be configured to maintain a measurement geometry in the presence of adverse environmental conditions, such as flight environmental conditions, as described above. For example, the sensor may be on a vehicle such as an aircraft, and housing 260 may be configured to maintain the alignment of light source 210 and light detector 220 during baseline illumination detection during takeoff, landing, and during flight. Housing 260 may be further configured to protect the quartz lining of sample gas tube 206, conduits 234, and/or gas recirculation flow path 250 from breaking during adverse environmental conditions, or otherwise protect the quartz lining from mechanical stress associated with adverse environmental conditions. Housing 260 may further be configured to house and protect light source 210, light detector 220, controllers 214 and 224, sample gas tube 206, recirculation flow path 250, pump 240, valves 236 and 238, fluid inlet 230, and fluid outlet 232 from mechanical stress associated with the adverse environmental conditions.

The sensor may introduce a gas into the sample gas volume (306). For example, a controller, such as light source controller 214, light detector controller 224, and/or an external device in communication with gas-concentration sensor 200 via sensor interface 246, may cause valves 236 and 232 to open gas inlet 230 and gas outlet 232 to be in fluid communication with conduits 234 and close and/or shut off gas recirculation flow path 250 from in fluid communication with conduits 234. The controller may cause a pump to circulate air containing a gas, e.g., ozone, through gas inlet 230, conduits 234, sample gas tube 206, and gas outlet 232. In other examples, the controller may cause the pump to circulate air including ozone within conduits 232 and sample gas tube 206, e.g., so as to fill sample gas tube 206 with a concentration of ozone corresponding to, proportional to, and/or representative of the concentration of ozone within a volume of interest, such as the cabin of an aircraft. In some examples, gas-concentration sensor 200 may measure a concentration of ozone while the air is circulating, e.g., via illumination of sample gas tube 206 and detection of the illumination level of light after having propagated through sample gas tube 206. In some examples, the controller may cause the pump to substantially stop the flow of air including ozone within conduits 232 and sample gas tube 206, e.g., during a gas-concentration measurement.

The sensor may illuminate a sample gas volume and detect an illumination level with the gas present, e.g., a sample illumination level (308). For example, a controller, such as light source controller 214 and/or an external device in communication with light source 210 via sensor interface 246 may cause light source 210 to emit light into sample gas tube 206. A controller, such as detector controller 224 and/or an external device in communication with light detector 220 via sensor interface 246 may cause light detector 220 to measure an illumination level of sample gas tube 206, e.g., a sample illumination level with ozone present in sample gas tube 206. In some examples, the controller may receive a signal from light detector 220 proportional to the sample illumination level of sample gas tube 206 with ozone present, and the controller may store the sample illumination level in memory. In some examples, the sample illumination level may be detected during flight conditions. Housing 260 may be configured to maintain a measurement geometry in the presence of adverse environmental conditions, such as flight environmental conditions, as described above. For example, the sensor may be on a vehicle such as an aircraft, and housing 260 may be configured to maintain the alignment of light source 210 and light detector 220 during sample illumination detection during takeoff, landing, and during flight. Housing 260 may be further configured to protect the quartz lining of sample gas tube 206, conduits 234, and/or gas recirculation flow path 250 from breaking during adverse environmental conditions, or otherwise protect the quartz lining from mechanical stress associated with adverse environmental conditions. Housing 260 may further be configured to house and protect light source 210, light detector 220, controllers 214 and 224, sample gas tube 206, recirculation flow path 250, pump 240, valves 236 and 238, fluid inlet 230, and fluid outlet 232 from mechanical stress associated with the adverse environmental conditions.

The sensor, and/or an external device, may determine a gas-concentration based on the baseline illumination level and the sample illumination level (310). For example, gas-concentration sensor 200 may include processing circuitry and/or a processor and computer-readable storage medium encoded with instructions for determining an ozone concentration based on signals from light detector 220 proportional to baseline and sample illumination levels. In some examples, controller 224, controller 214, and/or an external device may determine an ozone concentration based on baseline and sample illumination levels.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described. These and other examples are within the scope of the following claims.

What is claimed is:

1. A method of measuring a gas concentration, the method comprising:
    illuminating, with a light source, a volume of space that includes a gas;
    measuring, with a detector, a first illumination level of the volume of space;
    removing, via a catalyst, the gas from the volume of space;
    measuring, with the detector, a second illumination level of the volume of space with the gas removed from the volume of space; and
    determining, via a processor, a gas concentration in the volume of space based on a comparison of the second illumination level of the volume of space and the first illumination level of the volume of space,
    wherein the volume of space is configured to be in fluid communication with a gas recirculation flow path including a catalyst, the catalyst configured to substantially remove the gas from the volume of space.

2. The method of claim 1, wherein the gas is ozone.

3. The method of claim 1, wherein the first illumination level comprises ultra-violet (UV) light and the light source comprises a UV light emitting diode (LED).

4. The method of claim 1, wherein the volume of space is defined by a gas housing configured to constrain the gas to flow through the volume of space.

5. The method of claim 4, wherein removing the gas from the volume of space comprises:
    closing one or more valves configured to shut off fluid communication between the gas housing, a fluid inlet, and a fluid outlet;
    opening one or more valves configured to open fluid communication between the gas housing and the recirculation path including the catalyst;

causing, via a pump, the gas to circulate within the volume of space and the recirculation path including the catalyst; and removing the gas via chemical reaction of the gas by the catalyst.

6. The method of claim 4, wherein the gas housing is configured to protect an inner surface of the gas housing from adverse environmental conditions.

7. The method of claim 6, further comprising:
maintaining a measurement geometry in the presence of adverse environmental conditions,
wherein a sensor housing is configured to house and protect the light source, the detector, the processor, the gas housing, the recirculation flow path, the pump, the one or more valves, the fluid inlet, and the fluid outlet from mechanical stress associated with the adverse environmental conditions.

8. The method of claim 7, wherein the adverse environmental conditions comprise flight environmental conditions.

9. The method of claim 8, where the adverse environmental conditions comprise at least one of a vibration, an air pressure, and an acceleration force.

10. The method of claim 4, wherein the gas housing comprises an ozone inert material, where in the ozone inert material is light reflecting for the illumination from the light source.

11. The method of claim 10, wherein the ozone inert material comprises quartz.

12. A gas-concentration measurement system comprising:
an ultra-violet (UV) illumination source configured to illuminate a volume of space, wherein the volume is in fluid communication with a gas inlet and a gas outlet, wherein the gas inlet and the gas outlet are configured to allow a gas to flow through the volume;
a UV detector configured to measure an illumination level within the volume; and
a gas recirculation flow path configured to be in fluid communication with the volume of space and including a catalyst, the catalyst configured to remove the gas from the volume of space during measurement of the illumination of the volume.

13. The gas-concentration measurement system of claim 12, wherein the UV illumination source is a UV light emitting diode (UV LED).

14. The gas-concentration measurement system of claim 13, wherein the volume of space is defined by a sample gas tube.

15. The gas-concentration measurement system of claim 14, further comprising:

a first valve configured to switch fluid communication with the sample gas tube between the gas inlet and the gas recirculation flow path;
a second valve configured to switch fluid communication with the sample gas tube between the gas outlet and the gas recirculation flow path; and
a pump configured to circulate the gas within the sample gas tube and gas recirculation flow path.

16. The gas-concentration measurement system of claim 14, further comprising:
a sensor housing configured to house the UV LED, the UV detector, the gas recirculation flow path, and the sample gas tube, wherein the sensor housing is further configured to protect the UV LED, the UV detector, the gas recirculation flow path, and the sample gas tube from adverse environmental conditions.

17. The gas-concentration measurement system of claim 16, wherein the adverse environmental conditions include environmental conditions associated with flight including at least one of vibration, an atmospheric pressure less than 700 hPa, a temperature less than 50 degrees Fahrenheit, and an acceleration force greater than or equal to 1.5 g.

18. The gas-concentration measurement system of claim 12, wherein the sample gas tube comprises an ozone inert material that is UV reflective.

19. A gas-concentration measurement system comprising:
a light source configured to illuminate a volume of space including a gas;
a light detector configured to measure an amount of light from the light source after the light has propagated through a portion of the volume of space including the gas,
wherein the light source is an ultra violet (UV) light emitting diode (LED), wherein the light detector is a UV detector, and wherein the light is UV light; and
a catalyst configured to remove the gas from the volume during measurement of the light from the light source;
a gas housing defining the volume of space and configured to provide a flow path for the gas, wherein the gas housing is configured to protect an inner surface of the gas housing from degradation during flight environmental conditions; and
a sensor housing configured to house the UV LED, the UV detector, the gas housing, and the catalyst, wherein the sensor housing is configured to maintain a measurement geometry during flight environmental conditions.

20. The gas-concentration measurement system of claim 19, wherein the sample gas tube comprises an ozone inert material that is UV reflective.

* * * * *